US009717532B2

(12) United States Patent
Refai (10) Patent No.: US 9,717,532 B2
(45) Date of Patent: Aug. 1, 2017

(54) ARTICULATING SPINAL ROD SYSTEM

(71) Applicant: REFAI TECHNOLOGIES, LLC, Atlanta, GA (US)

(72) Inventor: Daniel Refai, Atlanta, GA (US)

(73) Assignee: REFAI TECHNOLOGIES, LLC, Atlanta, GA (US)

( * ) Notice: Subject to any disclaimer, the term of this patent is extended or adjusted under 35 U.S.C. 154(b) by 0 days.

(21) Appl. No.: 14/983,055

(22) Filed: Dec. 29, 2015

(65) Prior Publication Data
US 2016/0106470 A1 Apr. 21, 2016

Related U.S. Application Data

(63) Continuation of application No. 14/033,574, filed on Sep. 23, 2013, now Pat. No. 9,232,966.

(60) Provisional application No. 61/704,728, filed on Sep. 24, 2012.

(51) Int. Cl.
*A61B 17/70* (2006.01)

(52) U.S. Cl.
CPC ...... *A61B 17/7023* (2013.01); *A61B 17/7013* (2013.01); *A61B 17/7025* (2013.01); *A61B 17/7043* (2013.01); *A61B 17/7059* (2013.01); *A61B 17/7055* (2013.01); *Y10T 29/49826* (2015.01)

(58) Field of Classification Search
CPC ..... Y10T 403/32032; Y10T 403/32041; Y10T 403/32181; Y10T 403/32196; Y10T 403/32204; Y10T 403/32311; A61B 17/7023
See application file for complete search history.

(56) References Cited

U.S. PATENT DOCUMENTS

| 1,086,145 | A | | 2/1914 | Dodds | |
|---|---|---|---|---|---|
| 1,416,188 | A | | 5/1922 | Garman | |
| 2,103,988 | A | | 12/1937 | Le Bus | |
| 2,422,302 | A | | 6/1947 | Horn | |
| 2,479,339 | A | | 8/1949 | Gair | |
| 2,771,300 | A | | 11/1956 | Latzen | |
| 3,646,341 | A | * | 2/1972 | Klatskin | ................. F21L 11/00 362/268 |
| 3,949,699 | A | * | 4/1976 | Heese et al. | ............ B63B 35/70 114/249 |

(Continued)

*Primary Examiner* — Ellen C Hammond
*Assistant Examiner* — Stuart S Bray
(74) *Attorney, Agent, or Firm* — Heslin Rothenberg Farley & Mesiti P.C.; John W. Boger (57) ABSTRACT

An adjustable articulating spinal rod system including a first elongated element secured to a first bone, a second elongated element secured to the spine, and an articulating joint connecting the first and second elongated elements. The articulating joint including a first movable joint, a second movable joint, and at least one locking mechanism. The first movable joint is coupled to the first elongated element and the second movable joint which is also coupled the second elongate element. The first and second movable joints are configured to allow polyaxial movement and rotation of the first elongated element with respect to the second elongated element. The at least one locking mechanism immobilizes the first and second movable joints in the locked position to secure the first elongate element in a position relative to the second elongate element and allow movement and rotation in an unlocked position.

14 Claims, 9 Drawing Sheets

(56) References Cited

U.S. PATENT DOCUMENTS

| | | |
|---|---|---|
| 4,287,968 A | 9/1981 | Stensson et al. |
| 4,320,884 A | 3/1982 | Leo |
| 4,338,038 A | 7/1982 | Cloarec |
| 4,365,488 A | 12/1982 | Mochida et al. |
| 4,382,572 A | 5/1983 | Thompson |
| 4,475,546 A | 10/1984 | Patton |
| 4,491,435 A | 1/1985 | Meier |
| 4,704,043 A | 11/1987 | Hackman et al. |
| 4,767,231 A | 8/1988 | Wallis |
| 4,863,133 A | 9/1989 | Bonnell |
| 5,088,852 A | 2/1992 | Davister |
| 5,149,146 A | 9/1992 | Simoni |
| 5,348,259 A | 9/1994 | Blanco et al. |
| 5,383,738 A | 1/1995 | Herbermann |
| 5,419,522 A | 5/1995 | Luecke et al. |
| 5,473,955 A | 12/1995 | Stinson |
| 5,568,993 A | 10/1996 | Potzick |
| 5,609,565 A | 3/1997 | Nakamura |
| 5,626,054 A | 5/1997 | Rembert et al. |
| 5,795,092 A | 8/1998 | Jaworski et al. |
| 5,846,015 A | 12/1998 | Mononen |
| 5,943,919 A | 8/1999 | Babinski |
| 6,017,010 A | 1/2000 | Cui |
| 6,164,860 A | 12/2000 | Kondo |
| 6,220,556 B1 | 4/2001 | Sohrt et al. |
| 6,238,124 B1 | 5/2001 | Merlo |
| 6,352,227 B1 | 3/2002 | Hathaway |
| 6,568,871 B2 | 5/2003 | Song et al. |
| 6,767,153 B1 | 7/2004 | Holbrook |
| 7,179,009 B2 | 2/2007 | Stimpfl et al. |
| 7,300,028 B2 | 11/2007 | Vogt |
| 7,427,113 B2 | 9/2008 | Choi |
| 8,001,873 B2 | 8/2011 | Peng |
| 8,060,975 B2 | 11/2011 | Williams |
| 8,104,382 B2 | 1/2012 | Hu |
| 2002/0076265 A1 | 6/2002 | Yagyu |
| 2002/0094227 A1 | 7/2002 | Filipiak et al. |
| 2002/0098033 A1 | 7/2002 | Cardoso |
| 2002/0130234 A1 | 9/2002 | Jenkins et al. |
| 2002/0166935 A1* | 11/2002 | Carnevali ............ F16C 11/0604 248/276.1 |
| 2003/0016989 A1* | 1/2003 | Wentworth et al. . H02G 3/0468 403/56 |
| 2003/0068193 A1* | 4/2003 | El-Haw et al. ........ B60G 7/005 403/56 |
| 2003/0089831 A1* | 5/2003 | Salvermoser et al. . F16M 11/40 248/274.1 |
| 2003/0156893 A1* | 8/2003 | Takagi ................. F16L 27/023 403/128 |
| 2003/0165353 A1* | 9/2003 | Clausell .................... E04B 1/19 403/56 |
| 2003/0180088 A1* | 9/2003 | Carnevali ............... F16M 11/14 403/56 |
| 2003/0204915 A1* | 11/2003 | Colemen, Jr. .......... A45D 42/16 7/170 |
| 2005/0013658 A1* | 1/2005 | Muders et al. ...... F16C 11/0614 403/122 |
| 2005/0095058 A1* | 5/2005 | Biba et al. ............ F16C 11/106 403/56 |
| 2005/0123346 A1* | 6/2005 | Nakamura et al. ... F16B 7/0406 403/348 |
| 2005/0276656 A1* | 12/2005 | Lim ......................... F16C 7/02 403/56 |
| 2005/0288669 A1* | 12/2005 | Abdou ............... A61B 17/6433 606/246 |
| 2006/0149229 A1* | 7/2006 | Kwak ................ A61B 17/7023 606/256 |
| 2007/0093816 A1* | 4/2007 | Arnin ................. A61B 17/7043 606/86 A |
| 2007/0118121 A1* | 5/2007 | Purcell ............... A61B 17/7055 606/261 |
| 2007/0118122 A1* | 5/2007 | Butler ................ A61B 17/7023 606/86 A |
| 2007/0154254 A1* | 7/2007 | Bevirt .................... F16M 11/40 403/56 |
| 2007/0277815 A1* | 12/2007 | Ravikumar ............. A61B 90/57 128/99.1 |
| 2008/0056808 A1* | 3/2008 | Bevirt .................... F16M 11/40 403/56 |
| 2008/0093516 A1* | 4/2008 | Bevirt .................... F16M 11/40 248/181.1 |
| 2008/0195208 A1* | 8/2008 | Castellvi ............ A61B 17/7004 623/17.15 |
| 2009/0074504 A1* | 3/2009 | Morales Arnaez . F16C 11/0638 403/77 |
| 2009/0136290 A1* | 5/2009 | Persson ............... B60R 11/0252 403/125 |
| 2009/0157120 A1* | 6/2009 | Marino .............. A61B 17/7049 606/278 |
| 2010/0030224 A1* | 2/2010 | Winslow ............ A61B 17/7023 606/104 |
| 2010/0034579 A1* | 2/2010 | He ....................... F16C 11/0604 403/115 |
| 2010/0036423 A1* | 2/2010 | Hayes ................ A61B 17/7025 606/260 |
| 2010/0042152 A1* | 2/2010 | Semler ............... A61B 17/7004 606/250 |
| 2010/0063547 A1* | 3/2010 | Morin ................ A61B 17/7023 606/278 |
| 2010/0234892 A1* | 9/2010 | Mazda ................. A61B 17/705 606/276 |
| 2010/0302661 A1* | 12/2010 | Lee ........................... B60R 1/04 359/872 |
| 2010/0331886 A1* | 12/2010 | Fanger ............... A61B 17/7005 606/264 |
| 2011/0251646 A1* | 10/2011 | Karnezis ............ A61B 17/7007 606/278 |
| 2012/0083845 A1* | 4/2012 | Winslow ............ A61B 17/7007 606/264 |
| 2014/0088649 A1* | 3/2014 | Refai ................. A61B 17/7013 606/256 |
| 2014/0214083 A1* | 7/2014 | Refai ................. A61B 17/7019 606/256 |

* cited by examiner

ARTICULATING SPINAL ROD SYSTEM

CROSS-REFERENCE TO RELATED APPLICATIONS

This application is a continuation of U.S. application Ser. No. 14/033,574 filed Sep. 23, 2013, which issued as U.S. Pat. No. 9,232,966 on Jan. 12, 2016 and which claims priority benefit under 35 U.S.C. §119(e) of U.S. provisional application No. 61/704,728 filed Sep. 24, 2012, which are incorporated herein by reference in their entireties.

TECHNICAL FIELD

The present disclosure relates generally to articulating spinal rod systems, and specifically to an articulating spinal rod system that allows the elongated members to be angularly adjusted in multiple planes at an articulating joint. The articulating joint may include a proximal joint and a distal joint to properly align fixation members with a patient's cervical vertebra and occipital region, cervical-thoracic, thoracic-lumbar, lumbar-sacral spinal regions or in a patient's lumbopelvic spine.

BACKGROUND

During a posterior cervical stabilization procedure the surgeon generally places screws into the lateral mass of the cervical vertebral body followed by a titanium rod and set screws. The described posterior cervical stabilization procedure provides stabilization of the cervical spine to aid in fusion of one or more levels of the spine. One end section of the rod is occasionally anchored to a plate attached to the occipital region in a procedure called occipitocervical stabilization. In occipitocervical stabilization constructs, the rod is characterized by two sections—a first section that extends over the cervical spine and a second section that connects to the occipital plate at an angle relative to the first section.

In conventional occipitocervical fixation assemblies, the rod may be pre-bent before placement in the patient to form the angle between the first and second sections. Once the rod is bent it may be used to connect a screw or hook at a cervical vertebrae and an occipital plate. The screw or hook may be placed at C1, C2, C3 or any level caudally. Each rod must be customized for each patient's unique anatomy, thus one rod configuration may not be used for all patients. A number of variables vary from patient to patient including the angle between the first and second rod sections. Since each patient's anatomy varies a pre-bent rod may not match each patient's anatomy precisely when the rod is placed. Further adjustment of the pre-bent rod is therefore regularly required during placement of the fixation assembly and is generally performed intraoperatively.

Adjusting a rod prior to and/or during an operation can create stress on the rod which decreases the fatigue strength of the rod material. If the fatigue strength is reduced significantly, then the integrity of the rod can be compromised and pose a significant risk to the patient. In addition, it may be time consuming and cumbersome to bend a rod prior to or during an operation. The rod bending problems are experienced with occipitocervical fixation assemblies, as well as other spinal inflection points such as lumbopelvic spine fixation assemblies and other implant systems featuring elongated elements that are manually configured to conform to specific spatial requirements.

SUMMARY

The drawbacks of conventional implant systems, and the practice of bending and shaping elongated elements, can be avoided with articulating assemblies in accordance with the present invention.

Articulating assemblies in accordance with the invention may include an adjustable articulating assembly for implantation in a human or animal. The assembly may include a first elongated element for attachment to a first bone, and a second elongated element for attachment to a second bone. A coupling may connect the first and second elongated elements. The coupling may include a moveable joint configured to allow polyaxial movement of the first elongated element with respect to the second elongated element. The assembly may further include a locking mechanism. The locking mechanism may be operable in an unlocked condition to permit polyaxial movement of the first elongated element with respect to the second elongated element, and a locked condition to immobilize the movable joint and fix the position of the first elongated element with respect to the second elongated element.

The present disclosure relates generally to an articulating spinal rod system, and more specifically, to an articulating spinal rod system which may include articulating joints. In one aspect, provided herein is an articulating spinal rod system, including a first rod, a second rod, a first articulating joint system, and a second articulating joint system. The first rod includes a first elongated element and a second elongated element and the second rod includes a first elongated element and a second elongated element. The first articulating joint system is configured to couple the first elongated element and the second elongated element of the first rod. The second articulating joint system is configured to couple the first elongated element and the second elongated element of the second rod.

In another aspect, provided herein is an articulating joint mechanism including a first rod, a second rod, and a joint assembly configured to engage the first rod and the second rod.

In yet another aspect, provided herein is a method of assembling an articulating joint system, which includes obtaining a first elongated element and a second elongated element. The method may also include aligning a first spherical end with a distal end of the first elongated element, placing a first member and a second member of a conical receptacle over the first spherical end and the distal end of the first elongated element, and securing the first member to the second member to form a first joint. The method may further include aligning a second spherical end with a cavity of a receptacle, the receptacle is coupled to the first spherical end. The method also includes placing a cover element of the receptacle over the second spherical end and securing the cover element to the cavity to form a second joint. The method includes inserting a hinge member of a pivot assembly into a bearing member, the bearing member being attached to the second spherical end and inserting a pivot pin through the bearing member and the hinge member to rotatably couple the second elongated member to the bearing member.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

DETAILED DESCRIPTION OF EMBODIMENTS

Generally stated, disclosed herein is one embodiment of an articulating spinal rod system and an articulating joint mechanism. Further, a method of assembling an articulating joint system is discussed.

In this application, the words proximal, distal, anterior, posterior, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body.

Figure 1:
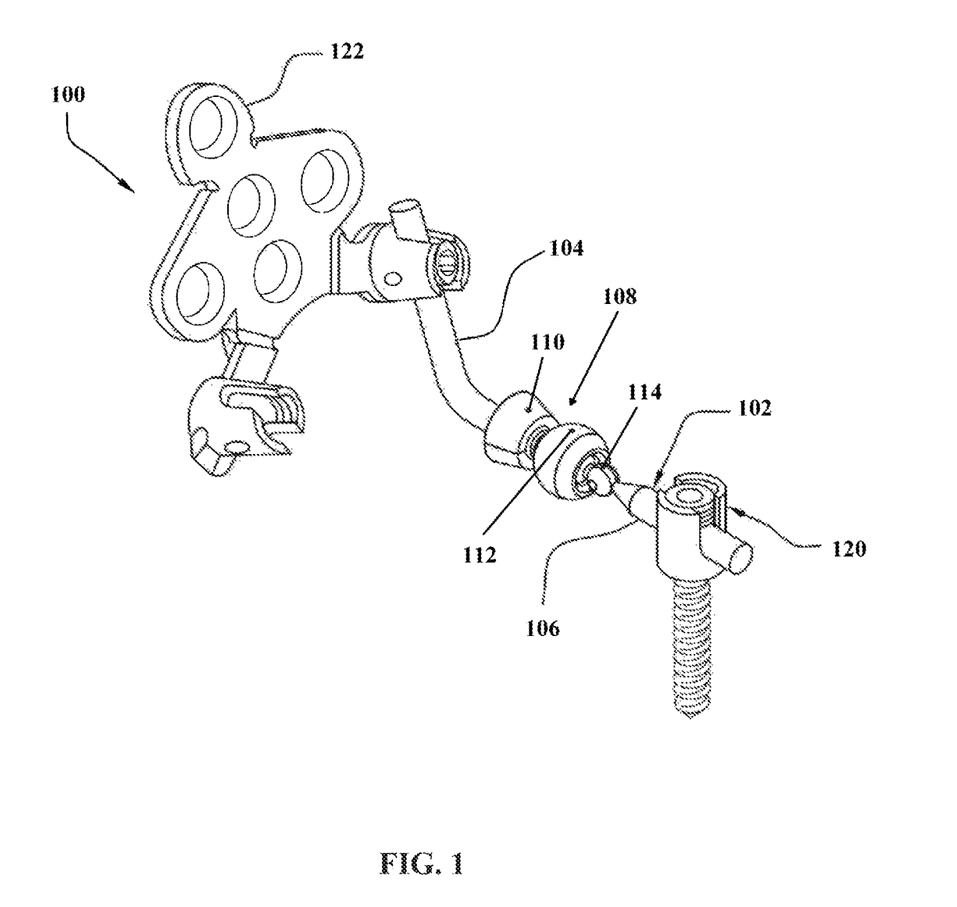
FIG. 1 is a truncated perspective view of an articulating spinal rod system, in accordance with an aspect of the present invention.
Figure 2:
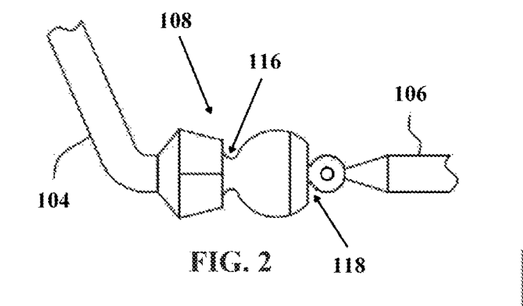
FIG. 2 is a truncated side view of the articulating spinal rod system of FIG. 1 in a first position, in accordance with an aspect of the present invention.
Figure 3:
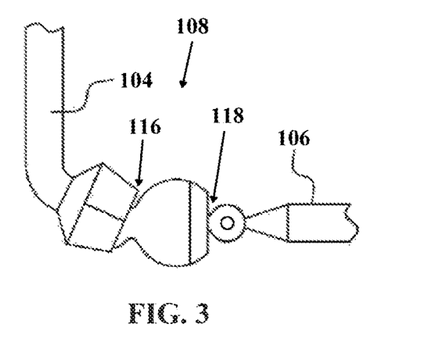
FIG. 3 is a truncated side view of the articulating spinal rod system of FIG. 1 with the proximal joint in a posterior position, in accordance with an aspect of the present invention.
Figure 4:
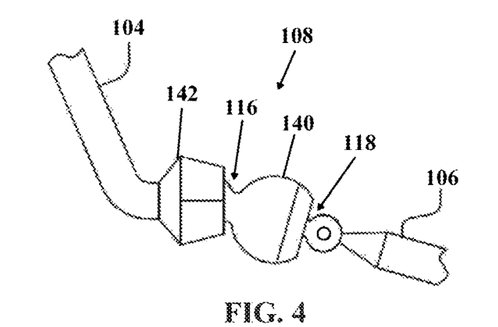
FIG. 4 is a truncated side view of the articulating spinal rod system of FIG. 1 with the proximal joint in an anterior position, in accordance with an aspect of the present invention.
Figure 15:
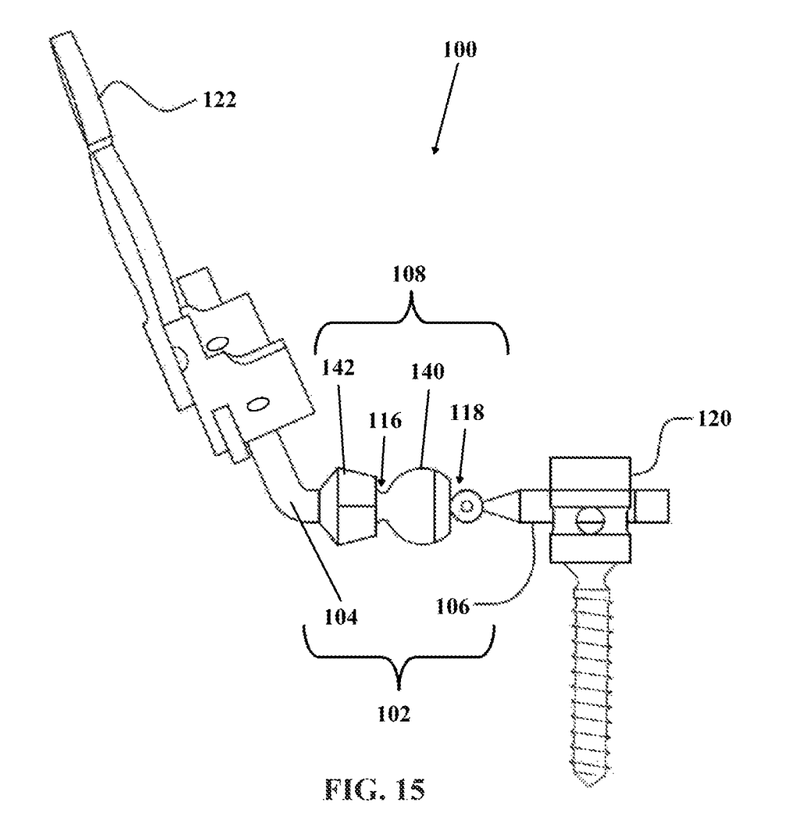
FIG. 15 is a truncated side view of the components of the articulating spinal rod system of FIG. 1, in accordance with an aspect of the present invention.
Figure 19:
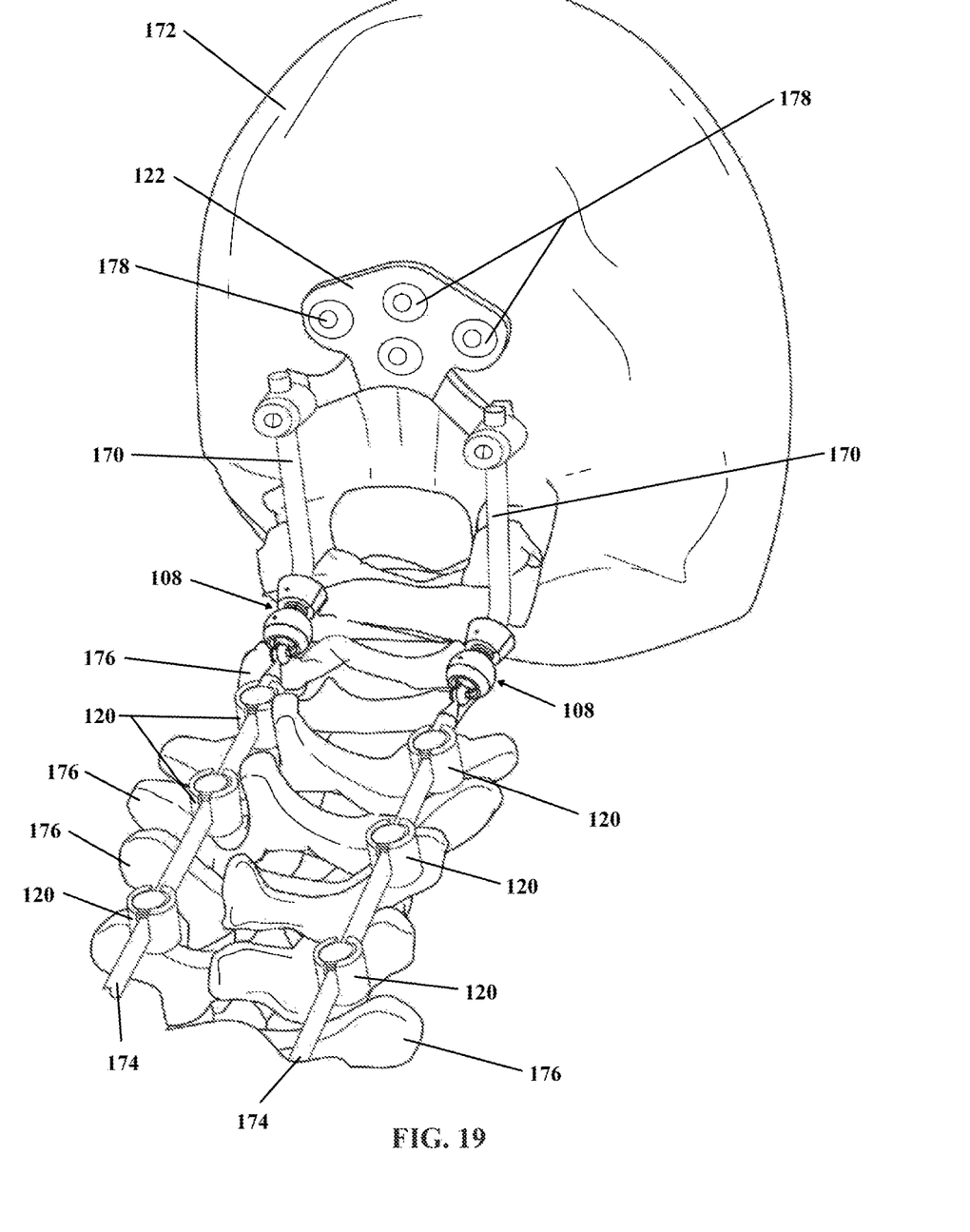
FIG. 19 is a front perspective view of the articulating spinal rod system of FIG. 1 attached to the skull and spine of a patient, in accordance with an aspect of the present invention.
Figure 20:
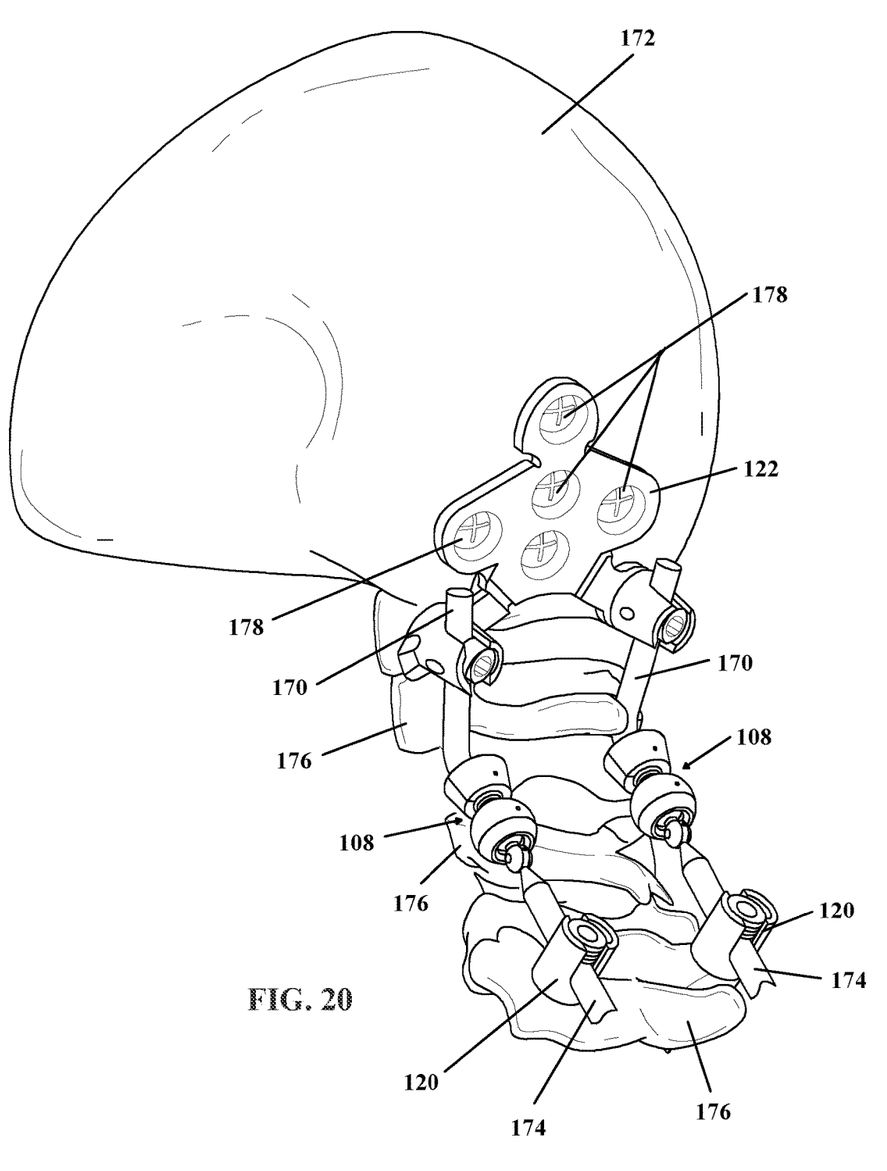
FIG. 20 is a side perspective view of the articulating spinal rod system of FIG. 1 attached to the skull and spine of a patient, in accordance with an aspect of the present invention.

Referring to the drawings, wherein like reference numerals are used to indicate like or analogous components throughout the several views, and with particular reference to FIGS. 1, 15, 19, and 20, there is illustrated a first exemplary embodiment articulating spinal rod system 100. The articulating spinal rod system 100 may be implanted into a human or an animal. The articulating spinal rod system 100, as shown in FIGS. 19 and 20, includes two rods 102 each including an articulating joint 108. In the illustrated embodiment, as shown in FIGS. 1 and 15, one of the two rods 102 is shown and the other is hidden for ease of viewing. The two rods 102 include a first elongated element 104 and a second elongated element 106. The articulating joint 108 connects the first elongated element 104 and the second elongated element 106. The first elongated element 104 is attached to a bone fixation device, for example, an occipital plate 122. The second elongated element 106 is secured to a screw assembly 120 and is truncated for clarity in the depicted embodiment. The second elongated element 106 may be longer and attached to the patient's spine with multiple anchors 120, such as hooks, screw assemblies, or the like. The second rod 102, not shown, may be configured identical to the rod 102 including the first elongated element 104 and the second elongated element 106 shown in FIG. 1 or in a different arrangement.

The articulating joint 108 is configured to allow for polyaxial movement of the first elongated element 104 with respect to the second elongated element 106. The articulating joint 108 may also include at least one locking mechanism, in the illustrated embodiment the articulating joint 108 includes a first locking mechanism 110, a second locking mechanism 112, and a third locking mechanism 114. The locking mechanisms 110, 112, and 114 may allow for polyaxial movement of the articulating joint 108 when in an unlocked condition and when in the locked condition the articulating joint 108 is immobilized and the positions of the first elongated element 104 and second elongated element 106 are fixed. The locking mechanisms 110, 112, and 114 may include at least one screw. The screw may include a tapered wedge portion.

Figure 16:
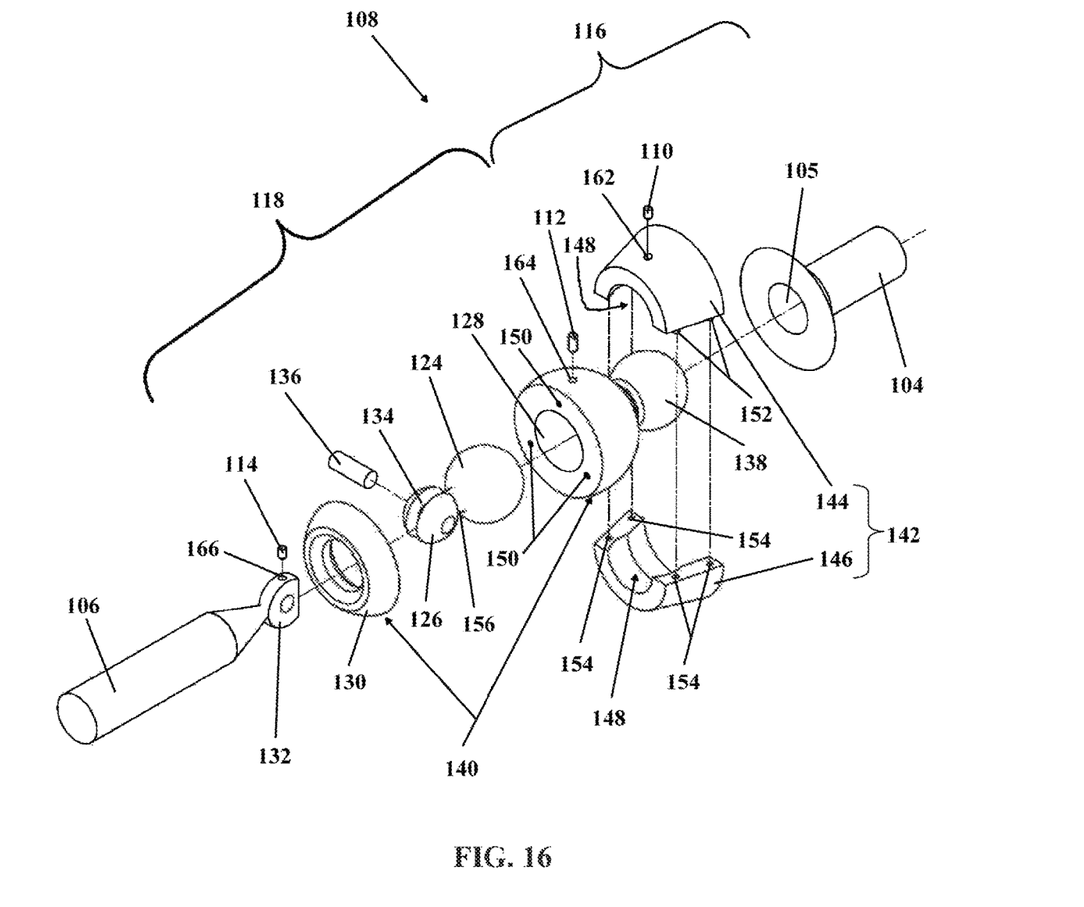
FIG. 16 is an exploded view of the joint of the articulating spinal rod system of FIG. 1, in accordance with an aspect of the present invention.

As illustrated in FIGS. 2-6 and 16, the articulating joint 108 includes at least one ball and socket joint. In the illustrated embodiment the articulating joint 108 includes two ball and socket joints, a first joint 116 and a second joint 118, which may be, for example, a proximal joint 116 and a distal joint 118. An exploded view of the articulating joint 108 is illustrated in FIG. 16, wherein the proximal joint 116 is connected to the first elongated element 104 and the distal joint 118 is connected to the second elongated element 106. The proximal joint 116 includes a first spherical ball end 138 inserted into a proximal receptacle 142. The first spherical ball end 138 may be, for example, a proximal ball. The proximal receptacle 142 includes a first member 144 fastened to a second member 146 to create a receptacle cavity 148. A distal end 105 of the first elongated element 104 may be secured between the first member 144 and the second member 146 to form a proximal end of the receptacle cavity 148. The first spherical ball end 138 may also be secured between the first member 144 and the second member 146 and slidingly engage the distal end 105 of the first elongated element 104. The fastening mechanisms used to secure the first member 144 and second member 146 may include snap fit fasteners, although other low profile fasteners are also contemplated. The snap fit fasteners include protrusions 152 and openings 154, in the depicted embodiment there are four protrusions 152 and four openings 154. The first spherical ball end 138 is coupled to a distal receptacle 140. The first spherical ball end 138 may be attached to a receptacle cavity 128 of the distal receptacle 140 created when a receptacle cover 130 is secured to the receptacle cavity 128.

The distal joint 118 includes a second spherical ball end 124 attached to a third spherical ball end or bearing member 126. The second spherical ball end 124 may be, for example, a distal ball. The terms "third spherical ball end" and "bearing member" may be used interchangeably herein. The second spherical ball end 124 and the bearing member 126 may be coupled together. The distal joint 118 also includes a receptacle cavity 128 for receiving the second spherical ball end 124 and a receptacle cover 130 for securing the second spherical ball end 124 in the receptacle cavity 128. The receptacle cover 130 is secured to a surface surrounding the receptacle cavity 128 to form a receptacle 140 using fasteners, such as press fit inserts, not shown, inserted into openings 150. The receptacle cavity 128 may include a rounded socket 128 adapted to receive the second spherical ball end 124 inside the receptacle 140. Further the distal joint 118 includes a pivot end or hinge member 132 on the second elongated element 106 which is inserted into an opening 134 in the bearing member 126. The terms "pivot end" and "hinge member" may be used interchangeably herein. A pivot pin 136 is inserted through the bearing member 126 and pivot end 132 to secure the second elongated element 106 to the distal joint 118. The pivot end 132 and pivot pin 136 form a pivot assembly.

Figure 5:
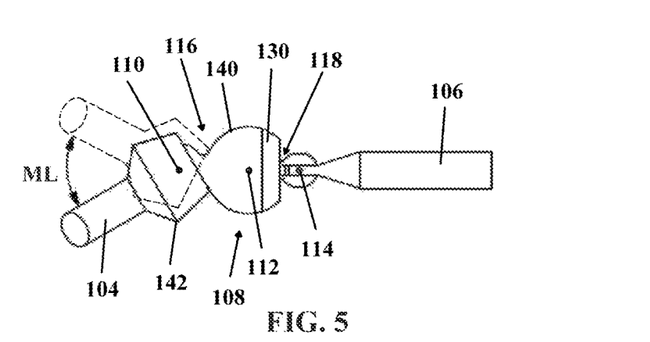
FIG. 5 is a truncated top view of the articulating spinal rod system of FIG. 1 showing the medial lateral motion of the proximal joint, in accordance with an aspect of the present invention.
Figure 6:
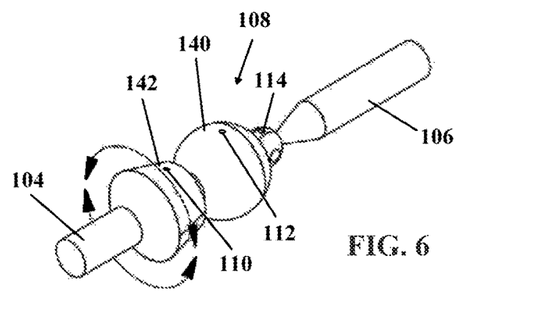
FIG. 6 is a truncated top isometric view of the articulating spinal rod system of FIG. 1 showing rotation of the proximal joint, in accordance with an aspect of the present invention.
Figure 7:
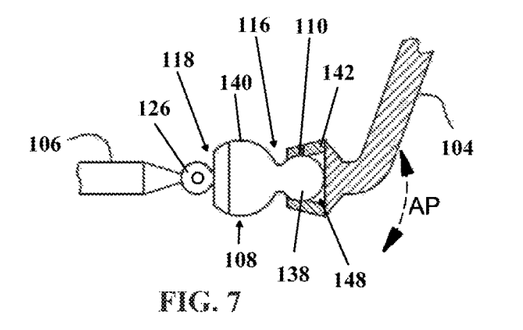
FIG. 7 is a truncated cross sectional side view of the articulating spinal rod system of FIG. 1, in accordance with an aspect of the present invention.
Figures 8, 9, 10:
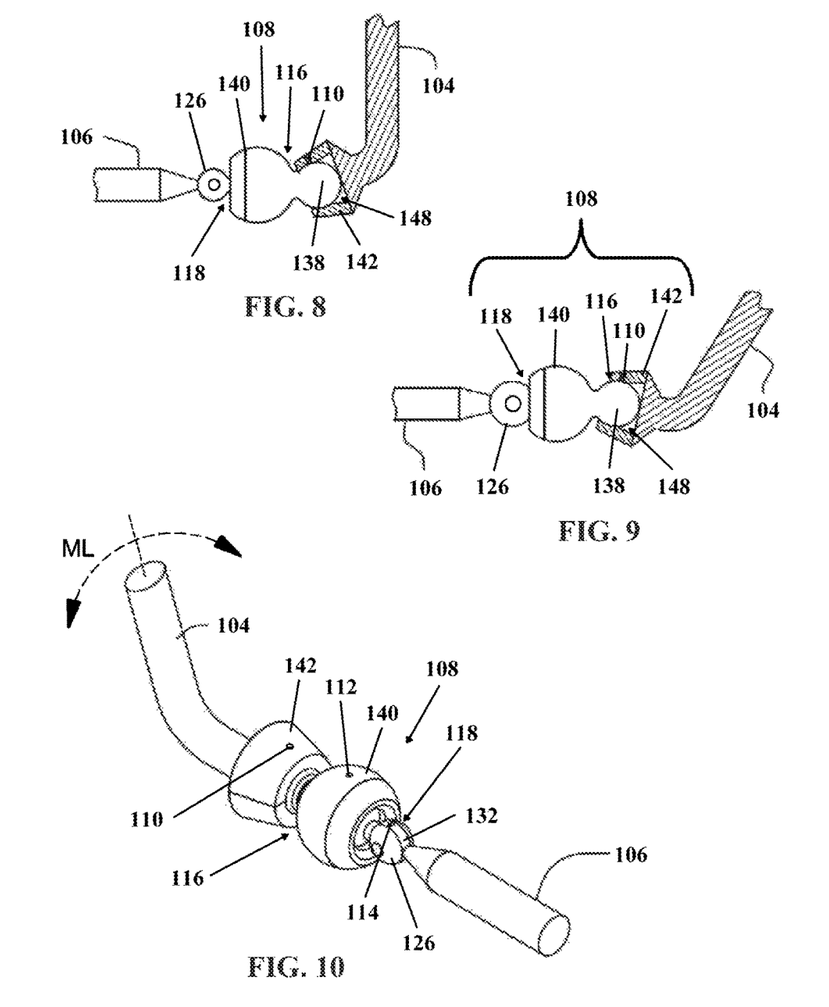
FIG. 8 is a truncated cross sectional side view of the articulating spinal rod system of FIG. 1 with the proximal joint in a posterior position, in accordance with an aspect of the present invention.
FIG. 9 is a truncated cross sectional side view of the articulating spinal rod system of FIG. 1 with the proximal joint in an anterior position, in accordance with an aspect of the present invention.
FIG. 10 is a truncated isometric view of the articulating spinal rod system of FIG. 1, in accordance with an aspect of the present invention.

Referring now to FIGS. 7-9, and with continued reference to FIGS. 1-6 and 16, the motion of the articulating joint 108 and the related angulations between the first elongated element 104 and second elongated element 106 are shown. The depicted articulating joint 108 is formed by two ball and socket joints, specifically, a proximal joint 116 and a distal joint 118. The proximal joint 116 allows the receptacle 140 to move polyaxially with respect to the proximal receptacle 142 and the connected first elongated element 104, and vice versa. In addition, the distal joint 118 allows the bearing member 126 to move polyaxially with respect to the distal receptacle 140, and vice versa. Further, the distal joint 118 allows the second elongated element 106 to move polyaxially with respect to the receptacle 140, and vice versa. The term "polyaxial" or "polyaxially," as used herein, refers to the ability of a first element to pivot or move in multiple planes with respect to a second element which the first element is coupled to. The receptacle 140 and the proximal receptacle 142 can pivot in multiple planes with respect to one another. The receptacle 140 and the second elongated element 106 can also move in multiple planes with respect to one another. The articulating joint 108 enables the first elongated element 104 and second elongated element 106 to pivot in multiple planes with respect to each other at both the proximal joint 116 and the distal joint 118.

As illustrated in FIGS. 2-4 and 7-9, the second elongated element 106 can pivot with respect to the first elongated element 104, and vice versa, in, for example, the sagittal plane at the proximal joint 116, as shown by arrows AP in FIG. 7.

Figures 11, 12:
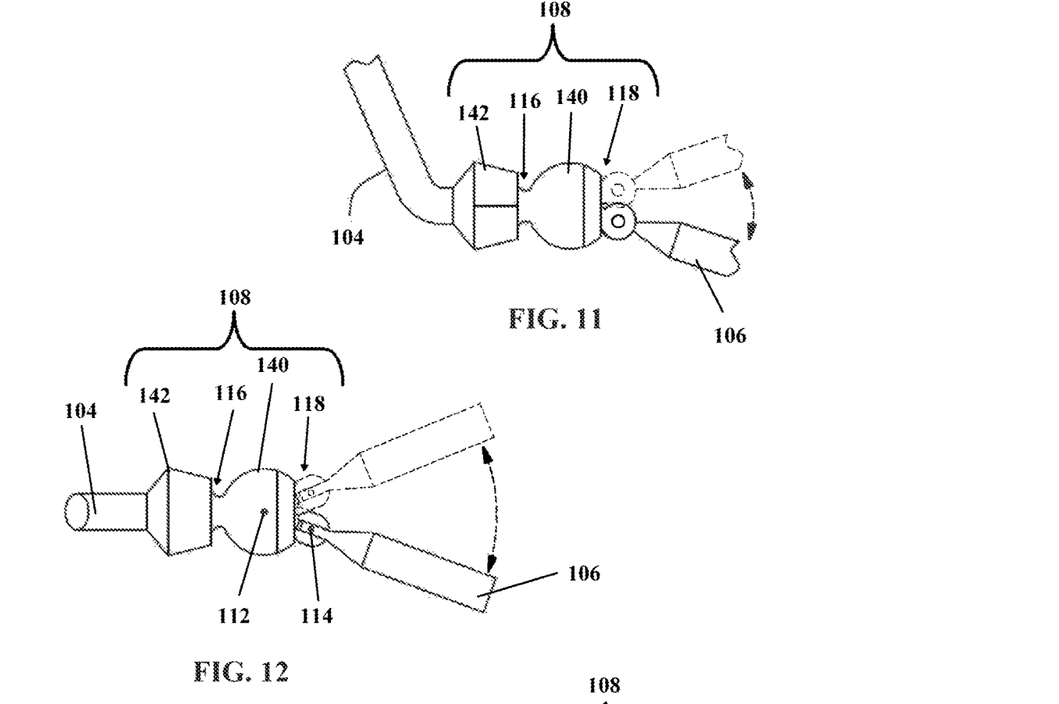
FIG. 11 is a truncated side view of the articulating spinal rod system of FIG. 1 showing anterior posterior movement of the distal joint, in accordance with an aspect of the present invention.
FIG. 12 is a truncated top view of the articulating spinal rod system of FIG. 1 showing the medial lateral movement of the distal joint, in accordance with an aspect of the present invention.
Figure 13:
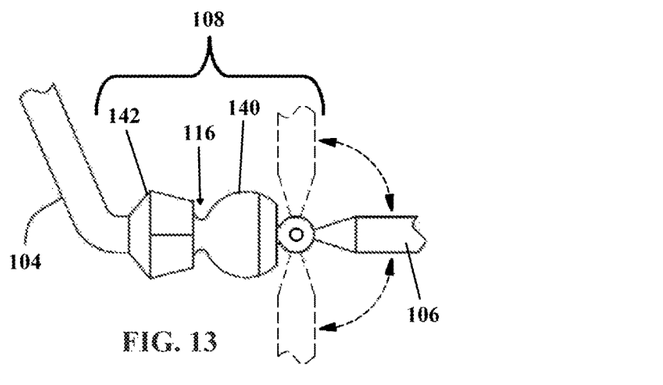
FIG. 13 is a truncated side view of the articulating spinal rod system of FIG. 1 showing the pivoting motion of the distal rod, in accordance with an aspect of the present invention.
Figure 14:
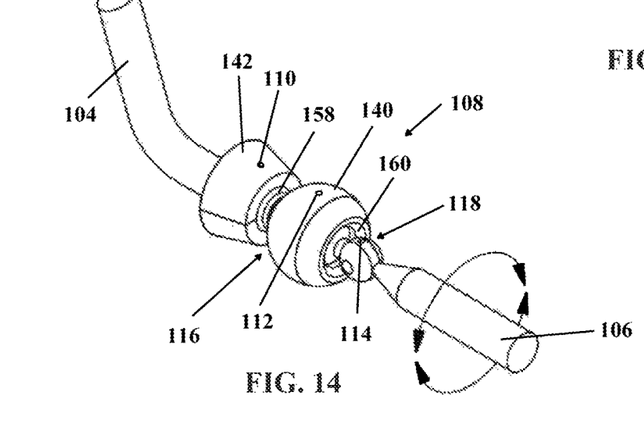
FIG. 14 is a truncated isometric view of the articulating spinal rod system of FIG. 1 showing the rotation of the distal joint, in accordance with an aspect of the present invention.

As depicted in FIGS. 5 and 10, the second elongated element 106 can pivot with respect to the first elongated element 104, and vice versa in a medial-lateral plane at the proximal joint 116, as shown by arrows ML in FIG. 10. In addition, the first elongated element 104 can rotate with respect to the second elongated element 106, and vice versa, at the proximal joint 116, as seen in FIG. 6. The second elongated element 106 can also rotate with respect to the first elongated element 104, and vice versa, at the distal joint 118, as illustrated in FIG. 14. FIG. 11 shows, the second elongated element 106 pivoting from a first position to a second position with respect to the first elongated element 104 in a sagittal plane at the distal joint 118. The second elongated element 106 can further pivot with respect to the first elongated element 104, and vice versa, in a medial-lateral plane at the distal joint 118, as illustrated in FIG. 12. As seen in FIG. 13, the second elongated element 106 may also pivot in a 180° range with respect to the receptacle 140, and vice versa. Since the second elongated element 106 rotates with respect to the receptacle 140, the second elongated element 106 may be moved in any direction.

An exploded view of the articulating joint 108 is shown in FIG. 16. A distal end of the first elongated element 104 coupled with the first member 144 and the second member 146 forms a receptacle cavity 148. The first spherical ball end 138 is adjacent to the receptacle cavity 148. The first spherical ball end 138 sits within the receptacle cavity 148 formed when the first member 144 and the second member 146 are attached together securing the distal end of the first elongate member 104 to the first and second members 144, 146. The first spherical ball end 138 is attached to the receptacle cavity 128 which has a generally cylindrical exterior. The receptacle cavity 128 mates with the second spherical ball end 124 which is attached to a bearing member 126. The second spherical ball end 124 is secured in the receptacle 140 by attaching the receptacle cover 130 to the receptacle cavity 128. The receptacle cover 130 is secured to the receptacle cavity 128 using fasteners, such as press fit inserts or the like, inserted into the openings 150. The second spherical ball end 124 is attached to the bearing member 126, in the depicted embodiment, for example, by a rod 156. In the depicted embodiment, the receptacle cover 130 passes over the bearing member 126 in order to secure the receptacle cover 130 to the receptacle cavity 128. The bearing member 126 includes a center opening 134 which mates with the pivot end 132 of the second elongated element 106.

The proximal receptacle 142 includes an enlarged opening 158, as shown in FIG. 14, which retains the first spherical ball end 138 and allows the receptacle 140 to pivot polyaxially through 36T of motion relative to the proximal receptacle 142 and the first elongated element 104, while being captively contained in the proximal receptacle 142. The enlarged opening 158 has a diameter smaller than the diameter of the first spherical ball end 138. The receptacle 140 includes an enlarged opening 160, as shown in FIG. 14, which retains the second spherical ball end 124 and allows the bearing member 126 to move polyaxially through 360° of motion relative to the receptacle 140 and the first elongated element 104, while being captively contained in the receptacle 140. The enlarged opening 160 has a diameter smaller than the diameter of the second spherical ball end 124. The pivot end 132 pivots at least 180° relative to the bearing member 126 within the openings 134 allowing the second elongated element 106 to be pivoted at least 180° relative to the first elongated element 104. The pivot end 132 has a diameter the same size or smaller than the diameter of opening 134.

Locking screws 110, 112, and 114, as shown in FIGS. 1 and 16, may be used to lock the components of the articulating joint 108 in the desired position. The locking screw 110 secures the first spherical ball end 138 in the desired position. The locking screw 112 secures the second spherical ball end 124 in the desired position. While locking screw 114 secures the pivot end 132 in the desired position. The locking screws 110, 112, and 114 may include external threads that engage internal threads in passages 162, 164, and 166, respectively. As such, locking screws 110, 112, and 114 may be movable in passages 162, 164, and 166 by threading the screws 110, 112, and 114 into the passages 162, 164, and 166 and axially rotating the screws 110, 112, and 114. The passages 162, 164, and 166 extend into the receptacle cavity 148, the receptacle cavity 128, and the opening 134, respectively. Locking screws 110, 112, and 114 are movable in passages 162, 164, and 166, respectively, between a locked position and an unlocked position.

In the locked position, as seen in FIGS. 2-4 and 7-9, the locking screw 110 (see FIGS. 7-9) engages the first spherical ball end 138 (see FIGS. 7-9), the locking screw 112 (see FIGS. 1 and 16) engages the second spherical ball end 124 (see FIG. 16) and the locking screw 114 (see FIGS. 1 and 16) engages the pivot pin 136 (see FIG. 16). When the locking screw 110 engages the first spherical ball end 138 in the locked position, the locking screw 110 compresses the first spherical ball end 138 in the receptacle cavity 148 (see FIGS. 7-9). When the locking screw 112 engages the second spherical ball end 124 in the locked position, the locking screw 112 compresses the second spherical ball end 124 in the receptacle cavity 128 (see FIG. 16). When the locking screw 114 engages the pivot pin 136 in the locked position, the locking screw 114 compresses the pivot pin 136. In these compressed conditions, frictional forces between the first spherical ball end 138, screw 110, and receptacle cavity 148 immobilize the ball end and prevent it from moving, so that the first elongated element 104 of rod 102 is locked in position relative to the receptacle 140. The frictional forces between the second spherical ball end 124, the screw 112, and receptacle cavity 128 immobilize the second spherical ball end 124 and prevent it from moving, so that the bearing member 126 is locked in position relative to the receptacle 140. The frictional forces between the bearing member 126, the screw 114, and the pivot end 132 immobilize the pivot end 132 and prevent it from pivoting, so that the second elongated element 106 of rod 102 is locked in position relative to the bearing member 126.

In the unlocked position, as shown in FIGS. 5-6 and 10, the locking screw 110 (see FIGS. 1 and 16) is positioned in the first passage 162 (see FIGS. 1 and 16) out of contact with the first spherical ball end 138 (see FIG. 16), leaving the first spherical ball end 138 free to move in the receptacle cavity 148 (see FIG. 16). This allows the receptacle 140 to move polyaxially relative to the proximal receptacle 142 and the first elongated element 104. In the unlocked position, as seen in FIGS. 11-12 and 14, the locking screw 112 (see FIGS. 12 and 14) is positioned in the second passage 164 (see FIG. 16) out of contact with the second spherical ball end 124 (see FIG. 16), leaving the ball end 124 free to move in the receptacle cavity 128 (see FIG. 16). This allows the bearing member 126 (see FIG. 16) and the second elongated element 106 to pivot polyaxially relative to the receptacle 140 and the first elongated element 104. In the unlocked position, as shown in FIG. 13, the locking screw 114 (see FIG. 16) is positioned in the third passage 166 (see FIG. 16) out of contact with the pivot pin 136 (see FIG. 16), leaving the pivot end 132 free to move in the opening 134 (see FIG. 16). This allows the second elongated element 106 to pivot relative to the bearing member 126 (see FIG. 16).

In an alternative locking arrangement, the locking screws 110, 112, and 114, may be replaced with locking screws which include wedge portions, not shown, which extend into the receptacle cavity 148, receptacle cavity 128, and opening 134, respectively, and engage the first spherical ball end 138, ball end 124, and pivot end 132. The locking screws with the wedge portions will lock and unlock the first spherical ball end 138, ball end 124, and pivot end 132 with respect to the receptacle cavity 148, receptacle cavity 128, and opening 134, respectively, as discussed above with reference to locking screws 110, 112, and 114. Further alternative locking elements may be used in place of the locking screws 110, 112, and 114 and the alternative locking elements can be non-threaded elements, such as a simple shim which is physically pushed into the receptacle cavity 148, receptacle cavity 128, and opening 134 against the first spherical ball end 138, ball end 124, and a pivot end 132, respectively, to prevent the first spherical ball end 138, ball end 124, and a pivot end 132 from pivoting in the receptacle cavity 148, receptacle cavity 128, and opening 134. The locking elements may be removable from the receptacle cavity 148, receptacle cavity 128, and opening 134, or contained in the wall of the receptacle cavity 148, receptacle cavity 128, and opening 134, respectively. In addition, more than one locking screw 110, 112, and 114 may be used in each of the receptacle cavity 148, receptacle cavity 128, and opening 134 to secure the first spherical ball end 138, ball end 124, and a pivot end 132, respectively, in the desired position.

The articulating joint 108 allows for multi-planar rotation permitting angular adjustment of the first elongated element 104 and second elongated element 106 not only in the anterior-posterior direction and sagittal plane but also in the medial-lateral direction. Different ranges of motion may be desired in multiple directions and are possible with the 360° of motion at the proximal joint 116, 360° of motion at the distal joint 118, and at least 180° of pivotal motion at the pivot end 132. The range of motion for the proximal joint 116 and distal joint 118 may be altered by changing the size and shape of the enlarged openings 158, 160. In addition, the range of motion for the pivot end 132 may be altered by changing the size and shape of the enlarged opening 160 or alternatively by pivoting the distal joint 118 to a different position. Further altering the enlarged openings 158, 160 to have alternative shapes, which may be symmetrical or asymmetrical, to provide different ranges of motion is also contemplated.

The distal receptacle 140 and the proximal receptacle 142 may have various inner and outer geometries, dependent upon the patient and the location of the articulating spinal rod system 100. Moreover, the distal receptacle 140 and the proximal receptacle 142 may include one or more gripping locations allowing for the surgeon to grasp and easily pivot the proximal joint 116 and distal joint 114. The articulating joint 108 and the rods 102 may include markings designating measurements for assisting the surgeon in adjusting the articulating joint 108 to position the first elongated element 104 and second elongated element 106 in a desired position.

While the embodiments presented have been described in use with occipitocervical fixation assemblies, articulating spinal rod systems in accordance with the invention may be used in a variety of applications. For example, an articulating spinal rod system can be used to interconnect first and second rod sections that are implanted in the lumbar region of the spine. The first and second rod sections may be arranged in an offset configuration, with the articulating joint providing the desired offset between the rod sections.

Articulating spinal rod systems in accordance with the invention can also be used in a rod to rod connector construct. The articulating spinal rod systems can connect an existing fusion construct with another, to treat scoliosis, bone fractures or adjacent segment disease. The articulating spinal rod system 100 can be connected to an existing rod using the articulating assembly.

Articulating spinal rod system 100 in accordance with the invention may also be used in a variety of applications outside of spine surgery, such as, for example, hip surgery, including any applications where elongated members are connected to one another, or to other structures. It should be understood that assemblies in accordance with the invention need not be used with rods, as noted above. Articulating spinal rod systems 100 in accordance with the invention may feature elongated elements in the form of elongated plates, shafts, or any type of elongated body member.

The articulating spinal rod system 100 allows the angle of the rods 102 to be easily adjusted in multiple planes. The angular adjustment is done by moving two articulating joints, a proximal joint 116 and a distal joint 118, to position the second elongated element 106 in a desired position relative to the first elongated element 104, rather than bending the rod in the operating room. The articulating spinal rod system 100 allows for the adjustment of the rod 102 without creating notches or other like depressions/projections in the rod material. By adjusting the angle of the rod 102 in multiple planes, the rod 102 can be adjusted to not only match the patient's anatomy, but also meet additional spatial requirements necessitated by other components of the system or instrumentation.

Figure 17:
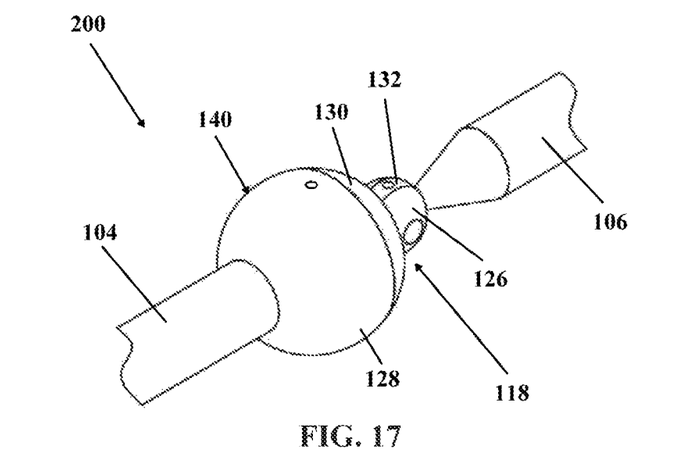
FIG. 17 is a truncated isometric view of an alternative joint embodiment of an articulating spinal rod system, in accordance with an aspect of the present invention.

FIG. 17 illustrates an articulating joint 200 shown in accordance with a second exemplary embodiment. The articulating joint 200 includes the distal joint 118 attached directly to first elongated element 104 at a proximal end and connected to the second elongated element 106 at the distal end. The distal joint 118 is of the type described above with reference to articulating joint 108. The articulating joint 200 includes a receptacle 140 with an enlarged opening 160 which retains the second spherical ball end 124 and allows the bearing member 126 to move polyaxially through 360° of motion relative to the receptacle 140 and the first elongated element 104, while being captively contained in the receptacle 140. The pivot end or hinge member 132 pivots at least 180° relative to the bearing member 126 within the opening 134 allowing the second elongated element 106 to be pivoted at least 180° relative to the first elongated element 104. The articulating joint 200 allows for the second elongated element 106 to move polyaxially with respect to the first elongated element 104, and vice versa, so the two elements can pivot in multiple planes with respect to one another. Thus, the second elongated element 106 can pivot with respect to first elongated element 104 in a sagittal plane and a medial-lateral plane as well as rotate 360°. In addition, the pivot end 132 allows the second elongated element 106 to pivot at least 180° relative to the bearing member 126.

Figure 18:
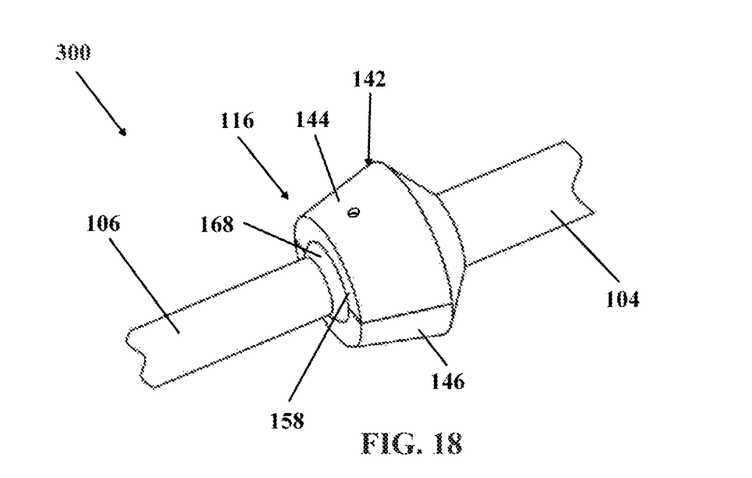
FIG. 18 is a truncated isometric view of another alternative joint embodiment of an articulating spinal rod system, in accordance with an aspect of the present invention.

A second exemplary embodiment of an articulating joint 300 is depicted in FIG. 18. The articulating joint 300 includes the proximal joint 116 attached to the first elongated element 104 at a proximal end and connected to the second elongated element 106 at the distal end by a ball 168. The ball 168 is inserted into the receptacle 142 created when the first member 144 is secured to the second member 146. The proximal joint 116 is of the type described above with reference to articulating joint 108. The articulating joint 300 includes a proximal receptacle 142 with an enlarged opening 158 which retains the ball 168 and allows the second elongated member 106 to pivot polyaxially through 360° of motion relative to the proximal receptacle 142 and the first elongated element 104, while being captively contained in the proximal receptacle 142. The ball 168 is coupled to the proximal end of the second elongated member 106. The articulating joint 300 allows for the second elongated element 106 to move polyaxially with respect to the first elongated element 104, and vice versa, so the two elements can pivot in multiple planes with respect to one another. Thus, the second elongated element 106 move with respect to first elongated element 104 in the sagittal plane and medial-lateral plane, as well as rotate 360°.

Referring now to FIGS. 19 and 20, the articulating spinal rod system 100 may include a first elongated element 170 connected to a first bone or anatomical region 172 and a second elongated element 174 connected to at least one vertebrae of the spine 176. As illustrated, an occipital plate 122 is secured to the first bone 172 using fasteners 178. The occipital plate 122 may be any occipital plate 122 which allows for the attachment of two rods 102. The first elongated elements 170 are coupled to the occipital plate 122 at a proximal end and to the articulating joint 108 at a distal end. The second elongated elements 174 are coupled to the articulating joint 108 at a proximal end and to a plurality of screw assemblies 120 at a distal end. The screw assemblies 120 are fastened to at least one second vertebrae 176. In the depicted embodiment the first bone 172 is the patient's skull and the at least one vertebrae of the spine 176 is the cervical spine. The screw assemblies 120 are attached to the spine 176 at C2 through C7.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed:

1. An articulating joint, comprising:
   a receptacle, comprising:
      a first member; and
      a second member coupled to the first member to form an opening; and
   a pivoting member, comprising:
      a spherical ball end configured to be received within the opening of the receptacle;
      a bearing member coupled to the spherical ball end and extending away from the opening of the receptacle, the bearing member including a center opening; and
      a hinge member coupled to the bearing member and received within the center opening.

2. The articulating joint of claim 1, wherein the opening receives and is coupled to the pivoting member to allow for rotational movement of the pivoting member with respect to the receptacle.

3. The articulating joint of claim 2, wherein the spherical ball end of the pivoting member moves polyaxially through 360° of motion relative to the receptacle.

4. The articulating joint of claim 3, further comprising:
   at least one locking mechanism coupled to the receptacle and engaging the spherical ball end.

5. The articulating joint of claim 3, further comprising:
   a first elongated element coupled to the receptacle; and
   a second elongated element coupled to the spherical ball end.

6. The articulating joint of claim 1, wherein the first member of the receptacle comprises a receptacle cavity; and
   wherein the second member comprises a receptacle cover configured to couple to the receptacle cavity to form the opening for receiving the spherical ball end.

7. The articulating joint of claim 6, wherein the receptacle and the spherical ball end are configured to allow for rotational movement of the spherical ball end with respect to the receptacle in an unlocked position.

8. The articulating joint of claim 1, wherein the pivoting member further comprises:
   a pivot pin, wherein the pivot pin engages the hinge member and the bearing member to couple the hinge member to the bearing member and allow for pivotal movement of the hinge member with respect to the bearing member in an unlocked position.

9. The articulating joint of claim 8, further comprising:
   at least one locking mechanism coupled to the hinge member and engaging the pivot pin.

10. The articulating joint of claim 1, further comprising:
    a first elongated element coupled to the receptacle; and
    a second elongated element coupled to the hinge member of the pivoting member.

11. The articulating joint of claim 10, the articulating joint further comprising:
    a first movable orientation, wherein the second elongated element moves polyaxially through 360° of motion relative to the first elongated element, and wherein the hinge member pivots at least 180° relative to the bearing member; and
    a second locked orientation, wherein the second elongated element is fixed relative to the first elongated element.

12. The articulating joint of claim 1, wherein the spherical ball end and the bearing member are attached by a rod.

13. The articulating joint of claim 1, further comprising:
    at least one locking mechanism coupled to the receptacle and engaging the spherical ball end to lock the receptacle in position with respect to the spherical ball end.

14. The articulating joint of claim 1, wherein the spherical ball end moves polyaxially through 360° of motion relative to the receptacle, and wherein the hinge member pivots at least 180° relative to the bearing member.

* * * * *